US005376086A

United States Patent [19]
Khoobehi et al.

[11] Patent Number: 5,376,086
[45] Date of Patent: Dec. 27, 1994

[54] LASER SURGICAL METHOD OF SCULPTING A PATIENT'S CORNEA AND ASSOCIATED INTERMEDIATE CONTROLLING MASK

[76] Inventors: Bahram Khoobehi, 5024 Cleveland Pl., Metairie, La. 70003; Stephen D. Klyce; Marguerite B. McDonald, both of 2858 Cheser St., New Orleans, La. 70115; Sanan B. Shaibani, 1500 W. Esplanack Apt. 4-F, Kenner, La. 70065

[21] Appl. No.: 143,087
[22] Filed: Oct. 26, 1993
[51] Int. Cl.$^5$ .............................................. A61N 5/06
[52] U.S. Cl. .......................................... 606/4; 606/6; 606/5; 128/898
[58] Field of Search ................... 606/4, 5, 6; 128/898

[56] References Cited

U.S. PATENT DOCUMENTS

| | | | |
|---|---|---|---|
| 3,096,767 | 7/1963 | Gresser et al. | 606/17 |
| 4,732,148 | 3/1988 | L'Esperance, Jr. | 606/5 |
| 4,856,513 | 8/1989 | Muller | 606/5 |
| 4,911,711 | 3/1990 | Telfair et al. | 606/5 |
| 4,917,486 | 4/1990 | Raven et al. | 606/4 |
| 4,994,058 | 2/1991 | Raven et al. | 606/5 |
| 5,207,668 | 5/1993 | L'Esperance, Jr. | 606/5 |
| 5,219,343 | 6/1993 | L'Esperance, Jr. | 606/5 |
| 5,312,320 | 5/1994 | L'Esperance, Jr. | 606/5 |

FOREIGN PATENT DOCUMENTS 0372127  6/1990  European Pat. Off. .............. 606/4

OTHER PUBLICATIONS

Steven E. Wilson, M.D., Stephen D. Klyce, PH.D.; "Advances in the Analysis of Corneal Topography"; Jan.-Feb., 1991; pp. 269-277.

*Primary Examiner*—Stephen C. Pellegrino
*Assistant Examiner*—Sonya C. Harris
*Attorney, Agent, or Firm*—Pravel, Hewitt, Kimball & Krieger

[57] ABSTRACT

A laser (e.g., excimer laser) and masking apparatus performs controlled sculpting of eye surfaces, such as corneal surfaces. The masking system includes a single/multi-layer (e.g., metallic) coated substrate (e.g., fused silica) with multiple openings in the substrate of desired size, shape and spacing to control the power transmission of a laser used in conjunction with the mask. The power transmission is controlled through the use of diffraction and absorption. The power transmission can be attuned to a particular surface by using topographical information of the surface in question. The surgeon can observe the topographical information and then pattern the openings (size, number, shape, spacing) so that reshaping can be done with greater intensity (using larger or more openings) to remove more corneal tissue in areas that the surgeon feels need more reshaping. Areas that need less reshaping can be masked complete by not placing holes or openings in that area of the mask, or by placing fewer or smaller openings.

9 Claims, 4 Drawing Sheets

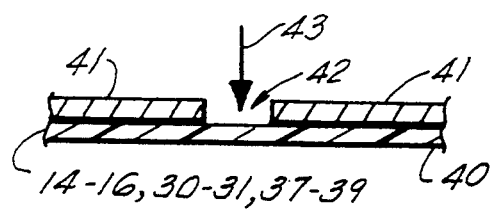
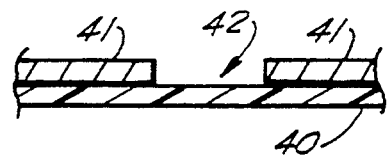
FIG. 5     FIG. 6
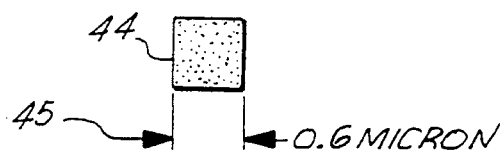
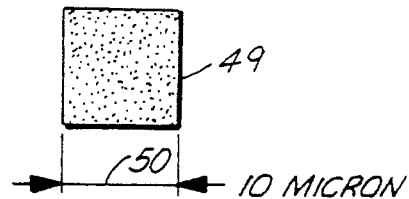
FIG. 7     FIG. 8
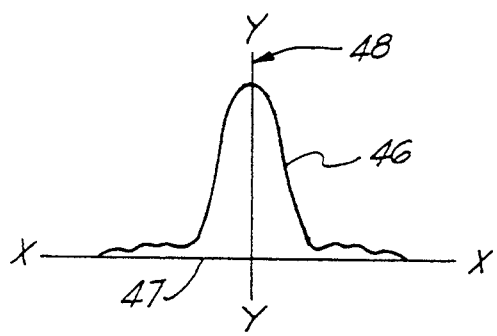
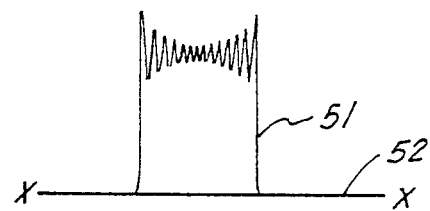
FIG. 9     FIG. 10

LASER SURGICAL METHOD OF SCULPTING A PATIENT'S CORNEA AND ASSOCIATED INTERMEDIATE CONTROLLING MASK

BACKGROUND OF THE INVENTION

1. Field of the Invention

The present invention relates to an improved laser surgical method and more particularly relates to an improved method of reshaping or sculpting the outer surface of a patient's cornea wherein a masking system includes a single or multi-layer coated substrate used to control the power transmission of a laser that is used in conjunction with the masking system. More particularly, the present invention relates to a laser surgery masking system for sculpting a patient's cornea using a mesh constructed to control power distribution through its substrate, preferably in the form of a grid having defined variable sized patterns etched through a reflective substrate over a transparent or translucent material (e.g. fused silica) wherein the pattern can be etched onto a deposited metal coating or other reflective or totally absorbent coating.

2. General Background

The corneal tear/air interface is the major refracting surface in the eye with an average convergent refractive power of 48.8 D. The human cornea has an average thickness of about 0.52 mm, and a transmittance cutoff wavelength of 300 nm. In recent years considerable advancement in low wavelength lasers has opened frontiers in refractive surgery.

Corneal topography can be used to estimate deformations and abnormalities of the corneal surface prior to refractive surgery. Low wavelength lasers could make refractive surgery a cost effective and common surgical procedure.

Various surgical techniques have been proposed for reprofiling of the corneal surface. One common technique is radial keratotomy in which a set of four to eight radial incisions are made in the eye to flatten the curvature of the cornea.

Another suggested technique employed the use of a low wavelength excimer laser to perform controlled ablative photodecomposition. Although altering the curvature of the outer corneal surface has been effective in correcting spherical myopia, the limitation with current laser technology is the inadequacy of corrective surgery in aspheric, irregularly astigmatic corneal surfaces.

Some patents have been issued which relate generally to the sculpting of a patient's cornea. For example, U.S. Pat. No. 4,911,711 entitled "Sculpting Apparatus for Correcting Curvature of the Cornea" provides ultraviolet-laser sculpting of the cornea to achieve optical correction through a newly shaped anterior surface. The apparatus subjects the laser beam to certain shaping and homogenizing operations prior to any attempt to specially characterize the beam for a particular sculpting procedure. In a preferred embodiment, the shaping and homogenizing operations present a tolerably homogeneous beam of enlarged dimension, so that specialty-characterizing may proceed on a dimensional scale that is greater than the corresponding dimension of ultimate surgical delivery to the eye, thereby enabling greater control of the quality of specialty characterizing. Provision is made for selectively monitoring the quality of the homogeneity and/or the specially characterized beam, with further provision for automatic cutoff of laser beam delivery to an eye in the event that quality is not within the predetermined limits of tolerance. And preferably, all beam shaping, homogenizing and characterizing operations proceed in a controlled environment which precludes ozone development and thus minimizes the beam degrading effect of ozone and particulates or other contaminants.

U.S. Pat. No. 4,994,058 entitled "Surface Shaping Using Lasers" issued to Anthony Raven et al. provides a laser system and masking apparatus for reprofiling surfaces, such as corneal surfaces. The system includes a laser and a mask disposed between the laser and the surface to be reprofiled, the mask providing a predefined profile of resistance to laser radiation, such that upon irradiation, part of the radiation is selectively absorbed and part is transmitted to the surface in accordance with the masked profile, to selectively erode the surface. The masking apparatus disclosed is a mask to be affixed to the surface, or may include a support structure to support and position the mask above the surface. The resistance profile is stated as created by varying the thickness or the composition of the mask.

SUMMARY OF THE INVENTION

It is an object of this invention to provide an improvement whereby laser ablation techniques can be applied to surfaces such as a patient's cornea to correct ametropia, such as myopia, hyperopia, regular astigmatism in the presence of irregular astigmatism. It is the intention of this invention to achieve the above objective by controlling the laser's power density distribution over the given area in question by a mask placed between the laser and the surface of the cornea.

The controlling of the laser power density will be accomplished by using optical properties in diffraction, absorption, and/or phase shifting. By using diffraction and absorption theory, a mask will be constructed which uses a grating mesh to control the power distribution through the mask. The grating mesh consists of a number of varying size patterns etched through a reflective substrate in conjunction with other absorption or/and shifting layers.

Each pattern preferably consists of a number of holes of varying sizes, each hole acting like an individual laser source, distributing the laser power as a function of the hole's size, shape and overlaid coating(s). By summing the power output of each pattern over a given area, a predictable average power distribution can be generated.

When a coherent beam passes through an opening, the energy distribution can be characterized by spherical wavelets which combine to yield the disturbance at a distant point. The disturbance of the grating can be described using diffraction theory. Light incident to the grating will be diffracted into several orders as long as the wavelength of the incident light is smaller than grating size. Through control diffraction a mask can be developed to allow for controlled power transmission at the corneal surface.

By controlling the power distribution of the laser through the mask, the erosion/ablation rate will be controlled. A secondary absorption layer and/or phase shifting layer can be added to enhance power distribution characteristics. The effectiveness of the invention to control the power density distribution at the incident surface relies on topographical data information of the given surface in question.

Using computer aided design, for example, topographical data can be obtained to construct a transformation data structure to construct the grating mesh's patterns for use in the fabrication of the mask.

The mask preferably consists of a transparent or translucent substrate (e.g. fused silica) with the grating mesh etched into a deposited metal or other reflective or absorbing coating. A secondary phase shifting grating pattern can be deposited to improve the power density distribution of the mask.

To further improve power distribution, an absorption patterned layer can also be deposited. Each layer can have a different pattern. By using microelectronics fabrication methods, for example, the mesh patterns can be etched or deposited onto the mask. The mesh will use the topographical data as the controlling mechanism for the overall mask pattern.

There are a number of preferred stages in the construction of the mask. The first stage is the coating of a reflective material onto the mask. The second stage is the generation of the mesh's patterns using topographical data of the corneal surface in question. Topographical data can be obtained using computers as discussed, for example, in an article "Advances in the Analysis of Corneal Topography", Survey of Ophthalmology, Volume 35, Number 4, January–February 1991. The third stage is the etching/depositing of selected patterns onto the coated substrate.

Metals are most commonly used as the reflective material, but other reflective or absorbing materials may be use as the primary coating on the mask. The reflective materials are coated onto a suitable glass or quartz substrate by using known techniques such as vacuum deposition. It has been found that aluminum has the best reflective characteristics for most low wavelength lasers, although other coating materials can be used.

The mask will consist of numerous patterns, holes in the coating. The separation and size of each pattern can differ greatly depending upon the topography of the cornea to be reshaped. Each hole or pattern will act as a point source once the laser has penetrated the transparent substrate. By controlling the placement/size of the patterns in the reflective coating, the transmission rate or power density of the laser can be controlled at the incident surface. As the pattern's diameters approach the wavelength of the laser source, the power density associated with the pattern will be diffused over a larger area. This diffraction property will provide controlled continuity in ablation at the corneal surface when numerous patterns are grouped together. If the patters' dimensions and groupings do not correspond to the corneal surface in question, the energy distribution at the corneal surface will not be continuous. The lack of continuity in energy distribution will result in imprinting of the patterns on the cornea. This imprint will not be a problem if other methods are used to compensate for this effect.

Through the use of a secondary absorption layer(s) and/or a phase shifting layer, the imprinting of the grating mesh can be eliminated. The mesh can use multi-layer coatings to control the transmittance of the laser. When electromagnetic radiation passes through a homogeneous, isotropic, but absorbing material, its intensity can be reduced. By using optical physics, a relation between the internal transmittance of an absorbing material as a function of thickness can be found. Similarly, by controlling the thickness of a deposited layer as a function of the wavelength of the laser source, a shift in the phase of the light can be achieved. It is possible to control the power transmittance of the laser by varying the coating thickness of the absorption material, thus providing a continuous etching on the corneal surface in conjunction with the etched mesh pattern.

If the desired continuity in ablation at the corneal surface can not be achieved by the use of a single mask, complementary masks can be used. The complementary masks can either be used in parallel or in series. In the case of a series system, each mask can be placed in a carousel (FIG. 1) and rotated into position as needed. Alternatively, a prism system (FIG. 2) can be used to place multiple masks in parallel thus providing a greater control over the power density distribution.

PMMA samples have shown that by using the grating mask, the power transmission of the laser can be caused to predictably vary throughout the diameter of the laser beam. By using different mesh patterns, the cutting rate of the PMMA can be controlled as a function of the position and dimensions of the mesh pattern. This method thus provides laser surgery of an irregular corneal surface by allowing the filter or mask patten to control the cutting rate at the corneal surface.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIG. 5 is a fragmentary sectional view illustrating a portion of a mask used with the method and apparatus of the present invention;

FIG. 6 is a fragmentary sectional view of a mask portion used with the method and apparatus of the present invention;

FIG. 7 is a schematic view illustrating an exemplary unmasked portion of the mask of FIG. 5;

FIG. 8 is a schematic view illustrating an exemplary unmasked portion of the mask of FIG. 6;

FIG. 9 is a graphical representation of the mask illumination of FIGS. 5 and 7 showing laser intensity as transmitted to the patient's eye when using the mask of FIG. 5;

FIG. 10 is a graphical representation of the mask and illumination of FIGS. 8 and 10 showing laser intensity as transmitted to the patient's eye when using the mask of FIG. 6;

DETAILED DESCRIPTION OF THE PREFERRED EMBODIMENT

Figure 1:
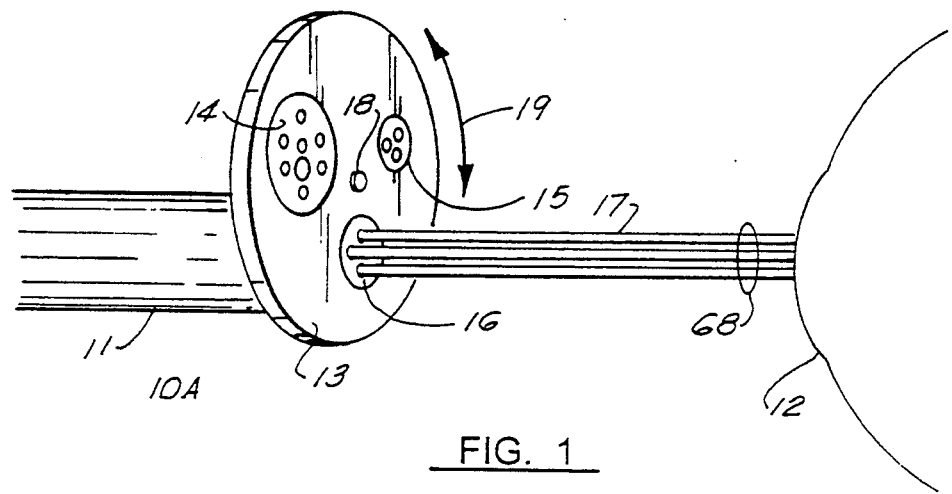
FIG. 1 is a schematic view illustrating a preferred embodiment of the apparatus of the present invention.

FIGS. 1–4 illustrate the method and apparatus of the present invention that is used to generate predictable laser intensity striking the surface of a patient's cornea, for reshaping the patient's cornea during eye surgery. In FIG. 1, the preferred embodiment is designated by the numeral 10A.

FIG. 1 shows laser beam 11 such as an excimer laser beam 11. The beam 11 strikes disk 13 which is rotatably mounted upon a spindle 18. A plurality of individual mask elements 14–16 are circumferentially spaced around the disk 13, as shown in FIG. 1. Each of the disks 14–16 provides a differing pre-selected placement of holes or openings, each hole or opening of differing size and shape.

By rotating the disk 13 about spindle 18 as shown by the curved arrow 19, the surgeon can sequentially irradiate a selected surface area of the patient's eye 12. A surgeon can first irradiate the patient's eye with an exit beam 17 that is transmitted through the mask 14. The surgeon can then rotate the disk 13 to the mask 15 and then irradiate the patient's eye with an exit beam 17 after the laser 11 irradiates the mask 15. A portion of the radiation passes through the holes or openings in the mask 14–16 as selected. The surgeon uses the third mask 16 as shown in FIG. 1 with the laser 11 striking the mask 16, the exit beam 17 striking the patient's eye 12. Lensing system 68 can be employed to focus the exit beam 17 if desired.

In this fashion, a different pattern and a different intensity of laser radiation strikes a selected area of the patient's eye 12 to produce a desired cumulative effect, i.e., the cumulation of laser irradiation that exits the masks 14, 15, and 16 in sequence.

Figure 2:
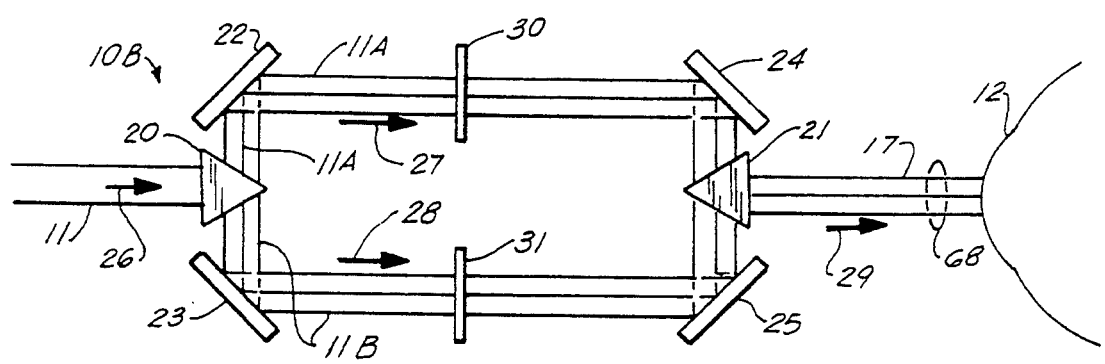
FIG. 2 is a schematic view illustrating a second embodiment of the apparatus of the present invention.

In the embodiment of FIG. 2, designated by the numeral 10B, laser beam 11 is transmitted to beam splitter 20. The laser beam 11 is split into left and right components 11A, 11B. The laser beam components 11A, 11B respectively strike reflective members 22, 23. The arrow 26 in FIG. 2 indicates the direction of travel of laser beam 11. The arrows 27, 28 indicate the direction of travel of the laser components 11A, 11B. Mask members 30, 31 in FIG. 2 are masks having a plurality of openings. The openings in masks 30 and 31 have a preselected number, shape, and placement of openings. In that regard, the mask elements 30, 31 are analogous to the differing mask elements 14–16 of FIG. 1.

Reflective members 24, 25 transmit the laser beam components 11A, 11B to beam splitter 21 wherein the laser beam combines to a single exit beam 17 that is transmitted to the patient's eye 12 and in the direction of arrow 29. Lensing system 68 can be used to focus the exit beam 17 as desired.

Figure 3:
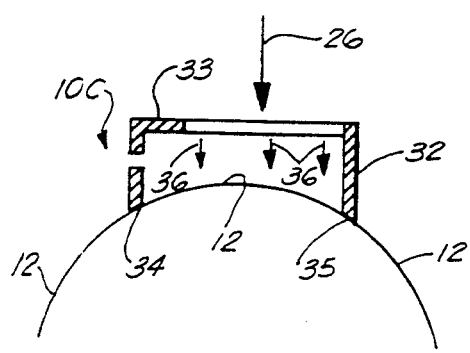
FIG. 3 is a schematic view illustrating a third embodiment of the apparatus of the present invention.

In the embodiment of FIG. 3, designated by the numeral 10C, a single mask 33 is maintained in a desired position relative to the patient's eye using support 32. The support 32 is of a size and shape and material so that the support rests directly upon the patient's eye 12 at positions 34, 35, as shown in FIG. 3. The incoming excimer laser beam is schematically illustrated by the arrow 26. After passing through the mask 33, the exit laser beam is schematically illustrated by the arrows 36 which show a diffused laser beam being transmitted to the selected surface area of the patient's eye 12.

Figure 4:
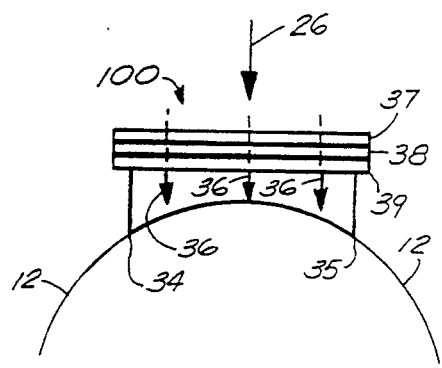
FIG. 4 is a schematic view of a fourth embodiment of the apparatus of the present invention.

In the embodiment of FIG. 4 designated by the numeral 10D, a plurality of layers 37–39 include fused silica substrate 39 and layers 37, 38, each layer with a separate pattern of holes that is used to control the power transmission that strikes the desired corneal surface. Each patterned layer 37, 38 (or additional patterned layers) can be manufactured, for example, using technology commonly employed for the manufacture of integrated circuits (microelectronics). Each of the layers 37–38 are coatings. By arranging multiple patterns 37, 38 (or more) as shown in FIG. 4, the surgeon can achieve a desired predictable exit laser beam transmission as indicated schematically by the arrows 36 in FIG. 4 which is the exit laser beam that strikes the patient's eye 12.

FIGS. 5–10 illustrate schematically the laser pattern generated by a single opening of selected size and shape on a particular mask element 14–16, 30–31, or 37–39. The mask element shown in FIGS. 5–6 provide a transparent support member 40 of glass or like transparent material coated with layer 41. Openings 42 have been formed in the layer 41.

FIGS. 5–6 illustrate two different size openings 42 for a mask member 14–16, 30–31, and 37–39. In FIG. 5, the opening 42 is smaller, e.g., 0.6 microns. In FIG. 6, the opening 42 is larger, e.g., 10 microns. Each opening 42 is square, but could be of a different selected shape. Each mask includes a transparent member such as fused silica layer 40 that is coated with a coating 41 that can be metallic. This can be an aluminized layer, for example.

An opening 42 is formed at a selected position in the layer 41 so that a transmitted beam 43 from a laser, such as an eximer laser, passes through opening 42 and to the patient's eye 12. The metalized layer 41 can be an absorbent or reflective layer that prevents passage of the laser beam therethrough. In FIG. 7, a pattern 44 is formed having a square configuration with a side dimension that is illustrated as 0.6 microns and by the number 45. In FIG. 9, a graphical representation of laser intensity, illustrated by the curve 46 is shown with reference to a zero intensity "y" axis 47 and with reference to a vertical or "y" axis 48 that is the geometric center of pattern 44.

In FIGS. 6, 8, and 10, a larger opening 42 provides a pattern 49 having a generally square configuration and with a side dimension 50 of 10 microns, for example. The graphical representation of FIG. 10 is illustrated by curve 51 wherein the X axis of zero intensity is schematically shown as the axis 52. A different intensity of exit laser is obtained for reshaping the patient's cornea by using a mask with a mesh of numerous of such openings 42, each having a selected size and shape and spacing on the mask 14–16, 30–31, 37–39. The laser is thus selectively diffused by the mask 114–16, 30–31, 37–39 and wherein each mask comprises a mesh having variable size and shape holes 42 over a selected area of the mask 14–16, 30–31, 37–39.

Figure 11:
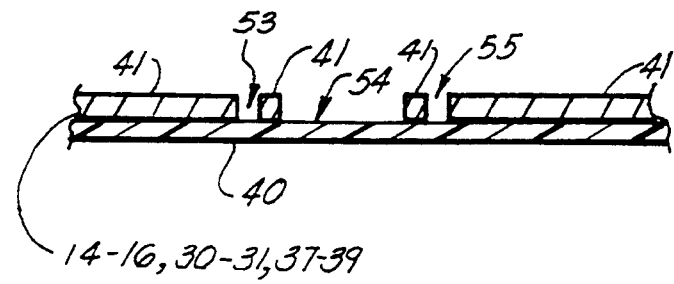
FIG. 11 is a fragmentary, sectional view illustrating a mask portion that can be used with the method and apparatus of the present invention.
Figure 12:
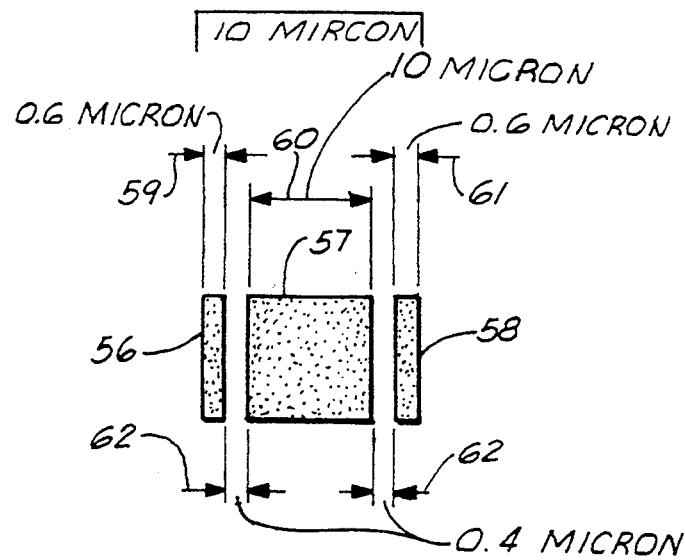
FIG. 12 is a schematic view illustrating an exemplary unmasked portion of the mask of FIG. 11.
Figure 13:
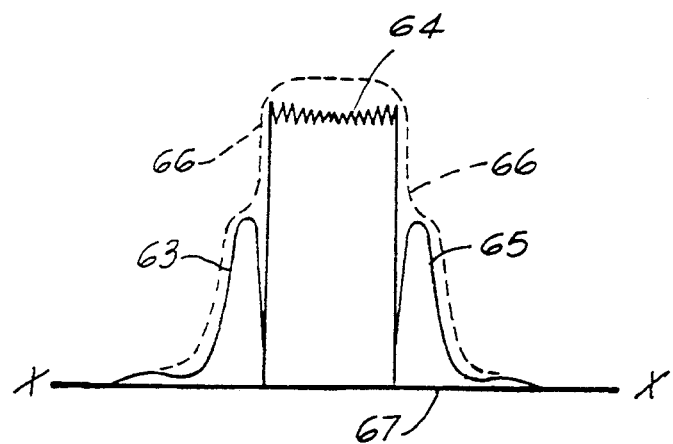
FIG. 13 is a graphical representation of the mask and illumination of FIGS. 11 and 12 showing laser intensity as transmitted to the patient's eye when using the mask of FIG. 11.

FIGS. 11–13 show the effect of a mask 14–16, 30–31, or 37–39 wherein a plurality of openings 53, 54, 55 are provided in coating 41.

In FIG. 12, patterns 56–58 show corresponding patterns for the laser beam as passing through the openings 53–55 respectively. In FIG. 12, the numerals 59–62 show dimension lines for the various opening or hole patterns 56–58.

Figure 14:
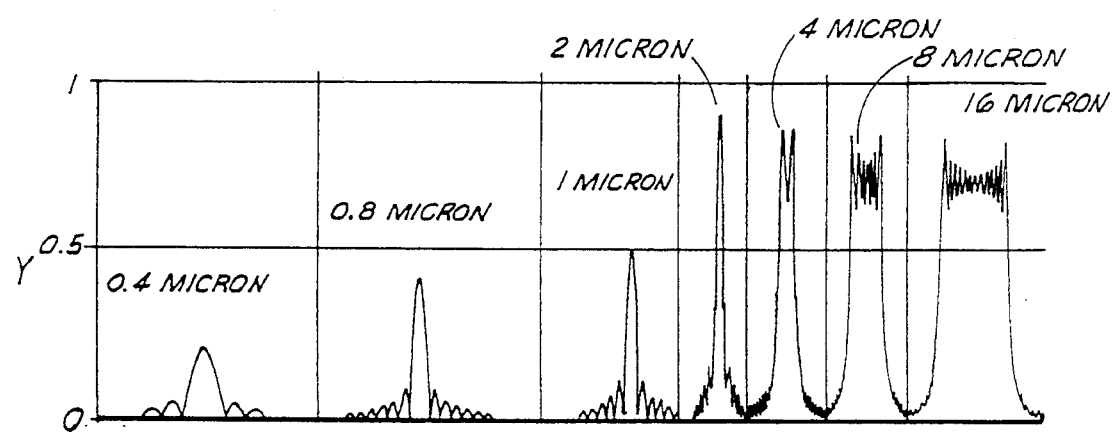
FIG. 14 is a schematic, graphical representation of laser intensities generated with mask opening of differing diameters.

In FIG. 13, a wave pattern 66 is shown as being a combination of the curves 63, 64, and 65 respectively being intensity curves generated by the respective patterns 56, 57, and 58. In FIG. 13, the zero or "X" axis is designated by the numeral 67. FIG. 14 shows various intensity graphs for corresponding square openings of various cross sectional dimensions as shown, wherein the zero or "X" axis is designated as 69 and the "Y" or intensity axis is designated as 70.

The power transmission can be attuned to a particular surface by using topographical information of the surface in question. Analysis of corneal topography using computers is a technique known in the art, described for example in an article entitled "Advances in the Analysis of Corneal Topography", Survey of Ophthalmology, Volume 35, Number 4, January–February 1991, incorporated herein by reference. The surgeon can observe the topographical information and then pattern the openings (size, number, shape, spacing) so that reshaping can be done with greater intensity (using larger or more openings) to remove more corneal tissue in areas that the surgeon feels need more reshaping. Areas that need less reshaping can be masked complete by not placing holes or openings in that area of the mask, or by placing fewer or smaller openings. The following table lists the part numbers and part descriptions as used herein and in the drawings attached hereto.

| PARTS LIST | |
|---|---|
| Part Number | Description |
| 10A | laser surgery masking apparatus |
| 10B | laser surgery masking apparatus |
| 10C | laser surgery masking apparatus |
| 10D | laser surgery masking apparatus |
| 11 | laser beam |
| 12 | patient's eye |
| 13 | mask disk |
| 14 | mask |
| 15 | mask |
| 16 | mask |
| 17 | laser beam exiting mask |
| 18 | spindle |
| 19 | curved arrow |
| 20 | beam splitter |
| 21 | beam splitter |
| 22 | reflective member |
| 23 | reflective member |
| 24 | reflective member |
| 25 | reflective member |
| 26 | arrow |
| 27 | arrow |
| 28 | arrow |
| 29 | arrow |
| 30 | mask |
| 31 | mask |
| 32 | support |
| 33 | mask |
| 34 | contact point |
| 35 | contact point |
| 36 | arrow |
| 37 | mask |
| 38 | mask |
| 39 | mask |
| 40 | fused silica |
| 41 | metallic coating |
| 42 | opening |
| 43 | laser beam |
| 44 | pattern |
| 45 | dimension line |
| 46 | intensity curve |
| 47 | zero intensity axis |
| 48 | center of transmitted beam |
| 49 | pattern |
| 50 | dimension line |
| 51 | intensity curve |

| -continued | |
|---|---|
| PARTS LIST | |
| Part Number | Description |
| 52 | zero intensity axis line |
| 53 | opening |
| 54 | opening |
| 55 | opening |
| 56 | pattern |
| 57 | pattern |
| 58 | pattern |
| 59 | dimension line |
| 60 | dimension line |
| 61 | dimension line |
| 62 | dimension line |
| 63 | intensity curve |
| 64 | intensity curve |
| 65 | intensity curve |
| 66 | cumulative curve |
| 67 | zero intensity axis |
| 68 | lens |
| 69 | zero intensity axis |
| 70 | intensity "Y" axis |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of reprofiling the surface of a patient's cornea comprising the steps of:
   a) locating a laser means relative to the surface of the patient's cornea, the laser means being operable to deliver laser radiation to the surface of the patient's cornea;
   b) placing a mask between the laser and the surface of the patient's cornea, the mask including a matrix of varying size holes for diffracting the laser beam;
   c) irradiating the mask whereby a portion of the radiation is selectively diffracted by the mask, wherein the mask comprises a mesh having a matrix of varying size holes spaced over a selected area of the mask; and
   d) wherein in step "c" the laser beam simultaneously hits the matrix of holes.

2. The method of claim 1 wherein the step of irradiating the mask includes reflecting a portion of the laser beam with a reflective material on a substrate material.

3. The method of claim 1 wherein the step of irradiating the mask includes reflecting a portion of the laser beam.

4. The method of claim 1 wherein the step of irradiating the mask includes reflecting a portion of the laser beam with a reflective material mounted on a fused silica substrate material.

5. The method of claim 1 wherein the step of irradiating includes reflecting a portion of the laser beam with a mask that has numerous patterns formed in a reflective coating.

6. The method of claim 1 further comprising splitting the beam into two or more components, and diffracting each component with a mask.

7. The method of claim 1 wherein there are two laser beams and further comprising the step of diffracting each beam with a mask.

8. The method of claim 1 wherein in step "b" there is provided a carousel with multiple masks, and further comprising the step of rotating a selected mask to diffract the laser beam.

9. The method of claim 1 further comprising the step of supporting the mask upon the patient's eye.

* * * * *